US012733868B2

(12) United States Patent
Lee et al.

(10) Patent No.: US 12,733,868 B2
(45) Date of Patent: Sep. 15, 2026

(54) DEPTH DATA-BASED PRESSURE ULCER DIAGNOSIS SYSTEM AND METHOD USING MULTISPECTRAL LIGHT SOURCE

(71) Applicant: INDUSTRY ACADEMIC COOPERATION FOUNDATION KEIMYUNG UNIVERSITY, Daegu (KR)

(72) Inventors: Jong-Ha Lee, Daegu (KR); Dong Bum Kim, Daegu (KR); Eun-Bin Park, Daegu (KR); Chan Il Kim, Daegu (KR)

(73) Assignee: INDUSTRY ACADEMIC COOPERATION FOUNDATION KEIMYUNG UNIVERSITY, Daegu (KR)

( * ) Notice: Subject to any disclaimer, the term of this patent is extended or adjusted under 35 U.S.C. 154(b) by 0 days.

(21) Appl. No.: 18/865,370

(22) PCT Filed: Oct. 14, 2023

(86) PCT No.: PCT/KR2023/015893
§ 371 (c)(1),
(2) Date: Nov. 13, 2024

(87) PCT Pub. No.: WO2024/117530
PCT Pub. Date: Jun. 6, 2024

(65) Prior Publication Data

US 2025/0311966 A1 Oct. 9, 2025

(30) Foreign Application Priority Data

Nov. 29, 2022 (KR) ........................ 10-2022-0163541

(51) Int. Cl.
*A61B 5/00* (2006.01)

(52) U.S. Cl.
CPC ............ *A61B 5/445* (2013.01); *A61B 5/0075* (2013.01); *A61B 5/4842* (2013.01)

(58) Field of Classification Search
CPC ....... A61B 5/445; A61B 5/0077; A61B 5/443; A61B 5/4842
See application file for complete search history.

(56) References Cited

U.S. PATENT DOCUMENTS 10,600,204 B1 * 3/2020 Rush ...................... A61B 5/746
2016/0157725 A1 * 6/2016 Munoz .................. H04N 23/51 600/407

(Continued)

FOREIGN PATENT DOCUMENTS

JP 2019505263 A 2/2019
JP 2021090763 A 6/2021

(Continued)

OTHER PUBLICATIONS

International search report of PCT/KR2023/015893, Mar. 28, 2024, English translation.

*Primary Examiner* — Gerald Johnson
(74) *Attorney, Agent, or Firm* — STIP Law Group, LLC

(57) ABSTRACT

The present invention provides a depth data-based pressure ulcer diagnosis system and method using a multispectral light source, the system comprising: a light emission unit for irradiating the skin of a body part with light in order to assess a pressure ulcer; a measurement unit which measures light transmittance using reflected light that is reflected from the skin of the body part when the skin of the body part is irradiated with light in order to assess a pressure ulcer; and a pressure ulcer diagnosis unit which assesses the state of a pressure ulcer on the basis of the light transmittance measured by the measurement unit, wherein the optical principle that the transmittance of light from a multispectral light (Continued)

source through the skin differs according to wavelength can be used to detect skin abnormalities caused by pressure ulcers.

16 Claims, 5 Drawing Sheets

(56) References Cited

U.S. PATENT DOCUMENTS

2017/0224271 A1* 8/2017 Lachenbruch ....... A61B 5/4842
2023/0133795 A1* 5/2023 Hanks .................. A61B 5/7275
600/323

FOREIGN PATENT DOCUMENTS

KR 20120072701 A 7/2012
KR 20200115058 A 10/2020
KR 20220040448 A 3/2022

* cited by examiner

DEPTH DATA-BASED PRESSURE ULCER DIAGNOSIS SYSTEM AND METHOD USING MULTISPECTRAL LIGHT SOURCE

CROSS-REFERENCE TO RELATED APPLICATIONS

This application is the U.S. National Phase under 35 U.S.C. § 371 of International Application No. PCT/KR2023/015893, filed on Oct. 14, 2023, which in turn claims the benefit of Korean Application No. 10-2022-0163541, filed on Nov. 29, 2022, the disclosures of which are incorporated by reference into the present application.

TECHNICAL FIELD

The present disclosure relates to a depth data-based pressure ulcer diagnosis system and method using a multispectral light source and, more specifically, a depth data-based pressure ulcer diagnosis system and method using a multispectral light source, which enables to detect skin abnormalities caused by a pressure ulcer by using an optical principle of a difference in skin transmittance per wavelength of multispectral light sources.

BACKGROUND ART

In general, pressure ulcers (pressure sores and bedsores) refer to a condition where continuous pressure is applied to a part of the body while continuously sitting or lying in one position such that a problem with blood circulation (ischemia) is caused in that part and damage to the subcutaneous tissue (ulcer) is caused in that part. These pressure ulcers are more likely to occur in unconscious patients, immobile patients with cranial or spinal nerve injuries, critical patients, and patients with general weakness. In this way, pressure ulcers are pressure necroses that occur in areas in direct contact with a surface when a seriously ill patient lies in bed for a long time and are caused when the skin over the protruding bone is compressed with no movement for a long time such that the blood cannot circulate and the skin dies and decomposes owing to the lack of oxygen.

In addition, pressure ulcers can occur anywhere, but frequently occur in areas like bony prominences that are subjected to high pressure, such as the occipital, shoulder, buttocks (sacrum, ischium), greater trochanter (when lying on the side), heels, and shins. In the early stages of pressure ulcers, the skin in the area under pressure becomes red, subsequently, ulcers emerge in that area, and finally, skin necrosis proceeds.

FIG. 1 is a view showing skin condition of pressure ulcers according to classification stage of pressure ulcers. As shown in FIG. 1, pressure ulcers progress in four stages. In stage 1 of pressure ulcers, no skin damage is observed, but the skin is warm and firm. The skin continues to be red even after 5 minutes after the pressure is removed. When the pressure is relieved, the original state is returned and can be recovered by changing the position. In stage 2 of pressure ulcers, the skin is ruptured, and abrasions and blisters emerge. Edema is severe and pain occurs when the fatty layer is invaded. In this case, when the pressure is relieved, it can be recovered within 1-2 weeks. In stage 3 of pressure ulcers, necrosis occurs down to the subcutaneous tissue, and an exudate with a foul odor appears. There is no pain, but edema is severe and necrotic tissue is observed, and it takes several months to remove and recover the necrotic tissue. In stage 4 of pressure ulcers, there occurs extensive tissue necrosis over the muscles, bones, and supporting tissues (tendons, joints). Necrotic tissue is visible and surgical treatment (skin grafting, flap surgery, etc.) is required.

In addition, pressure ulcers appear partially in different degrees rather than the entire affected area is damaged to the constant extent. That is, even the same affected area can have different forms, ranging from stage 1 to stage 4, depending on the area. Therefore, appropriate treatment and treatment methods are required even for the same affected area. In particular, pressure ulcers vary in size and severity in the affected areas, so accurate diagnosis and application of appropriate treatment are necessary.

In this way, there are clear criteria for the diagnosis of pressure ulcers, but many of the diagnoses are determined by a confirmation according to the risk assessment system by the doctor's visual inspection. This is a diagnosis based on experience, and may show different diagnosis contents depending on the diagnosing person. Conventional methods that rely on the experience of the diagnosing person have the probability of misdiagnosis, so a data-based diagnosis system standardized for the grade of pressure ulcers is required. Korean Patent Application Publication No. 10-2012-0072701 is disclosed as a prior art document.

DISCLOSURE

Technical Problem

The present disclosure is proposed in order to solve the above problems of previously proposed methods, and the objective of the present disclosure is to provide a depth data-based pressure ulcer diagnosis system and method using a multispectral light source, which enables detecting skin abnormalities caused by a pressure ulcer by using an optical principle of a difference in skin transmittance per wavelength of multispectral light sources, by including a light emission unit for emitting light on the skin of the body part for assessing pressure ulcers, a measurement unit for measuring light transmittance using the reflected light reflected when the light emission unit emits light to the skin of the body part for assessing pressure ulcers, and a pressure ulcer diagnosis unit for assessing the state of pressure ulcers on the basis of the light transmittance measured in the measurement unit.

In addition, by detecting skin abnormalities caused by the pressure ulcer by using the optical principle of the difference in skin transmittance per wavelength of the multispectral light sources, another objective of the present disclosure is to provide a depth data-based pressure ulcer diagnosis system and method using a multispectral light source, which is capable of assessing pressure ulcers by quantitatively assessing the state of pressure ulcers to determine a progression stage through big data learning utilizing a difference in light transmittance on the basis of an optical principle that light has different characteristics per wavelength when penetrating the skin, and is capable of non-invasively assessing the depth of the pressure ulcer incidence.

Furthermore, by assessing pressure ulcers on the basis of depth data standardized for the grade of pressure ulcers based on the optical principle of the differences in skin transmittance per wavelength of multispectral light sources, another objective of the present disclosure is to provide a depth data-based pressure ulcer diagnosis system and method using a multispectral light source, where the progress degree of pressure ulcers can be represented in three dimensions, such that the probability of misdiagnosis of pressure ulcers can be reduced and the accuracy of pressure ulcer diagnosis can be further improved.

Technical Solution

A depth data-based pressure ulcer diagnosis system using a multispectral light source according to characteristics of the present disclosure for achieving the objectives described above, as the depth data-based pressure ulcer diagnosis system using the multispectral light source, is characterized to include a light emission unit for emitting light on the skin of a body part for assessing pressure ulcers, a measurement unit for measuring light transmittance using the reflected light reflected when the light emission unit emits light to the skin of the body part for assessing pressure ulcers, and a pressure ulcer diagnosis unit for assessing the state of pressure ulcers on the basis of the light transmittance measured in the measurement unit.

Preferably, the light emission unit may emit light to the skin of the body part for assessing pressure ulcers, and may be configured with a multi-wavelength light source device enabling a selective wavelength according to an absorption wavelength characteristic of biological tissues.

More preferably, the light emission unit may be configured with the multi-wavelength light source device enabling the selective wavelength according to the absorption wavelength characteristic of biological tissues, and may emit light with a wavelength of 600 to 900 nm.

Preferably, the light emission unit may be configured to include a light source unit for emitting multispectral light sources of wavelengths different from each other to the same skin area for assessing pressure ulcers, a body unit where the light source unit is disposed for emitting the multispectral light sources of wavelengths different from each other, and a controller for controlling light radiation of the light source unit disposed on the body unit for emitting the multispectral light sources of wavelengths different from each other.

More preferably, the measurement unit may measure the light transmittance using the reflected light reflected when the light emission unit emits light to the skin of the body part for assessing pressure ulcers and the light transmittance may be configured as depth data of skin characteristics per wavelength of the multispectral light sources.

Even more preferably, the measurement unit may be configured with a depth camera for measuring depth data of skin characteristics per wavelength of the multispectral light sources of the light emission unit.

Even more preferably, the pressure ulcer diagnosis unit may assess the state of pressure ulcers on the basis of the light transmittance measured in the measurement unit and may assess pressure ulcers from depth data where the state of pressure ulcers is quantitatively assessed to determine a progression stage through big data learning utilizing a difference in light transmittance.

Even more preferably, the pressure ulcer diagnosis unit may assess pressure ulcers by quantitatively assessing the state of pressure ulcers to determine a progression stage through big data learning utilizing the difference in the light transmittance and may non-invasively assess a depth of a pressure ulcer incidence.

A depth data-based pressure ulcer diagnosis method using a multispectral light source according to characteristics of the present disclosure for achieving the objective described above is characterized to include, as the depth data-based pressure ulcer diagnosis method using the multispectral light source, (1) a step of emitting light on the skin of a body part for assessing pressure ulcers by a light emission unit, (2) a step of measuring light transmittance by a measurement unit by using a reflected light reflected when the light emission unit emits light to the skin of the body part for assessing pressure ulcers, and (3) a step of assessing the state of pressure ulcers by a pressure ulcer diagnosis unit on the basis of the light transmittance measured in the measurement unit.

Preferably, the light emission unit may emit light to the skin of the body part for assessing pressure ulcers, and may be configured with a multi-wavelength light source device enabling a selective wavelength according to an absorption wavelength characteristic of biological tissues.

More preferably, the light emission unit may be configured with the multi-wavelength light source device enabling the selective wavelength according to the absorption wavelength characteristic of biological tissues, and may emit light with a wavelength of 600 to 900 nm.

Preferably, the light emission unit is configured to include a light source unit for emitting multispectral light sources of wavelengths different from each other to the same skin area for assessing pressure ulcers, a body unit where the light source unit is disposed for emitting the multispectral light sources of wavelengths different from each other, and a controller for controlling light radiation of the light source unit disposed on the body unit for emitting the multispectral light sources of wavelengths different from each other.

More preferably, the measurement unit may measure the light transmittance using the reflected light reflected when the light emission unit emits light to the skin of the body part for assessing pressure ulcers and the light transmittance may be configured as depth data of skin characteristics per wavelength of the multispectral light sources.

Even more preferably, the measurement unit may be configured with a depth camera for measuring depth data of skin characteristics per wavelength of the multispectral light sources of the light emission unit.

Even more preferably, the pressure ulcer diagnosis unit may assess the state of pressure ulcers on the basis of the light transmittance measured in the measurement unit and may assess pressure ulcers from depth data where the state of pressure ulcers is quantitatively assessed to determine a progression stage through big data learning utilizing a difference in the light transmittance.

Even more preferably, the pressure ulcer diagnosis unit may assess pressure ulcers by quantitatively assessing the state of pressure ulcers to determine a progression stage through big data learning utilizing the difference in the light transmittance and may non-invasively assess a depth of a pressure ulcer incidence.

Advantageous Effects

According to a depth data-based pressure ulcer diagnosis system and method using a multispectral light source proposed by the present disclosure, it may enable to detect skin abnormalities caused by a pressure ulcer by using an optical principle of a difference in skin transmittance per wavelength of multispectral light sources, by configuring to include a light emission unit for emitting light on the skin of the body part for assessing pressure ulcers, a measurement unit for measuring light transmittance using the reflected light reflected when the light emission unit emits light to the skin of the body part for assessing pressure ulcers, and a pressure ulcer diagnosis unit for assessing the state of pressure ulcers on the basis of the light transmittance measured in the measurement unit.

In addition, according to a depth data-based pressure ulcer diagnosis system and method using a multispectral light source of the present disclosure, it may be possible to assess pressure ulcers by quantitatively assessing the state of pressure ulcers to determine a progression stage through big data learning utilizing a difference in light transmittance on the basis of an optical principle that light has different characteristics per wavelength when penetrating the skin, to non-invasively determine the depth of the pressure ulcer incidence, by detecting skin abnormalities caused by the pressure ulcer by using an optical principle of a difference in skin transmittance per wavelength of multispectral light sources.

Furthermore, according to a depth data-based pressure ulcer diagnosis system and method using a multispectral light source of the present disclosure, the progress degree of pressure ulcer may be represented in three dimensions, such that the probability of misdiagnosis of pressure ulcers can be reduced and the accuracy of the pressure ulcer diagnosis can be further improved, by assessing pressure ulcers with depth data standardized for the grade of pressure ulcers based on an optical principle of a difference in skin transmittance per wavelength of multispectral light sources.

DESCRIPTION OF REFERENCE NUMERALS

Figure 1:
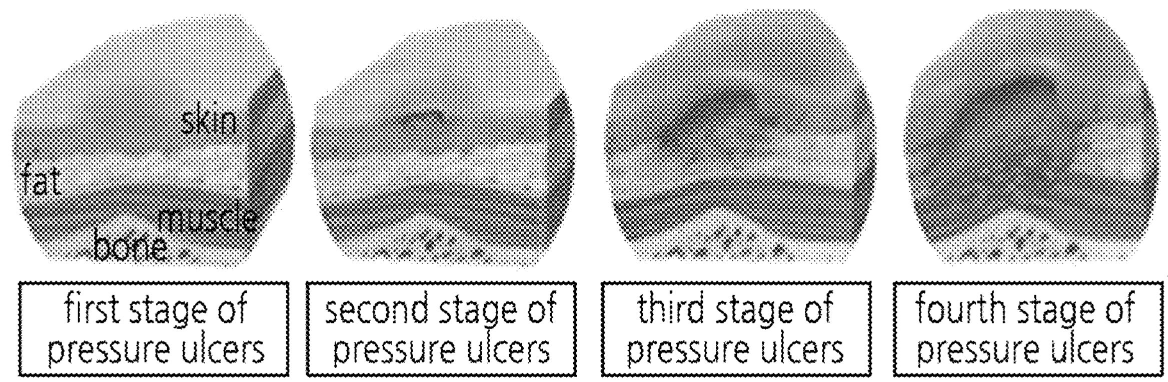
FIG. 1 is a view showing skin condition of pressure ulcers according to classification stage of pressure ulcers.

100: a pressure ulcer diagnosis system according to an exemplary embodiment of the present disclosure
110: a light emission unit
111: a light source unit
112: a body unit
113: a controller
120: a measurement unit
130: a pressure ulcer diagnosis unit
S110: a step of emitting light to the skin of the body part
S120: a step of measuring light transmittance using reflected light
S130: a step of assessing pressure ulcers

BEST MODE

Hereinafter, preferred exemplary embodiments will be described in detail with reference to the accompanying drawings so that those skilled in the art may easily implement the present disclosure. However, when describing the preferred exemplary embodiment of the present disclosure in detail, specific descriptions of relevant known features or configurations are omitted where it is deemed that such detailed descriptions would unnecessarily obscure the gist of the present disclosure. In addition, the same symbols are used for parts having similar functions and actions throughout the drawings.

In addition, when a part is "connected" to another part throughout the specification, it includes not only the case where it is "directly connected", but also the case where it is "indirectly connected" with another element in between. In addition, "including" a component means that it may further include other components, rather than excluding other components, unless specifically stated otherwise.

Figure 2:
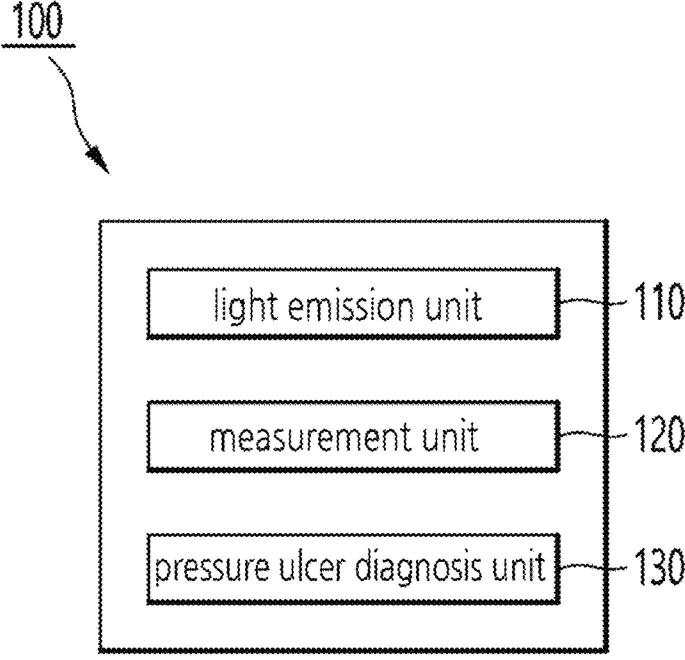
FIG. 2 is a view showing a configuration of a depth data-based pressure ulcer diagnosis system using a multispectral light source as a functional block according to an exemplary embodiment of the present disclosure.
Figure 3:
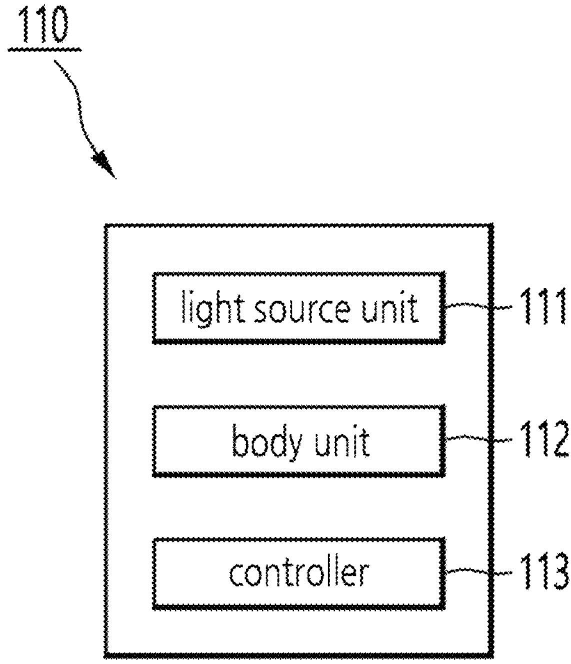
FIG. 3 is a view showing a configuration of a light emission unit of a depth data-based pressure ulcer diagnosis system using a multispectral light source as a functional block according to an exemplary embodiment of the present disclosure.
Figure 4:
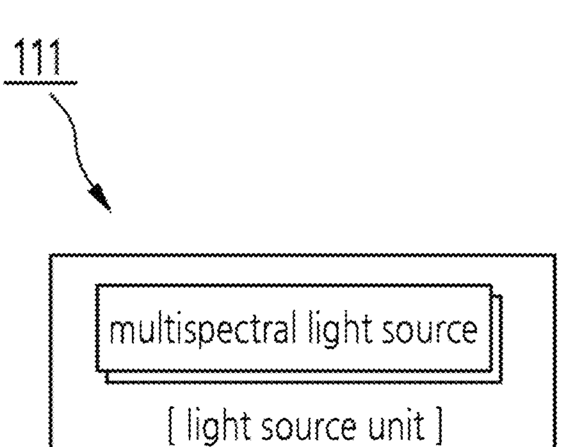
FIG. 4 is a view showing a configuration of a light source unit of a depth data-based pressure ulcer diagnosis system using a multispectral light source as a functional block according to an exemplary embodiment of the present disclosure.

FIG. 2 is a view showing a configuration of a depth data-based pressure ulcer diagnosis system using a multispectral light source as a functional block according to an exemplary embodiment of the present disclosure, FIG. 3 is a view showing a configuration of a light emission unit of a depth data-based pressure ulcer diagnosis system using a multispectral light source as a functional block according to an exemplary embodiment of the present disclosure, and FIG. 4 is a view showing a configuration of a light source unit of a depth data-based pressure ulcer diagnosis system using a multispectral light source as a functional block according to an exemplary embodiment of the present disclosure. As shown in FIGS. 2 to 4 respectively, the depth data-based pressure ulcer diagnosis system 100 using the multispectral light source according to an exemplary embodiment of the present disclosure may include a light emission unit 110 for emitting light on the skin of the body part for assessing pressure ulcers, a measurement unit 120 for measuring the light transmittance using the reflected light reflected when the light emission unit 110 emits light to the skin of the body part for assessing pressure ulcers, and a pressure ulcer diagnosis unit 130 for assessing the state of pressure ulcers on the basis of the light transmittance measured in the measurement unit 120. Hereinafter, a detailed configuration of the depth data-based pressure ulcer diagnosis system using the multispectral will be described in detail with reference to the accompanying drawings according to an exemplary embodiment of the present disclosure.

Figure 5:
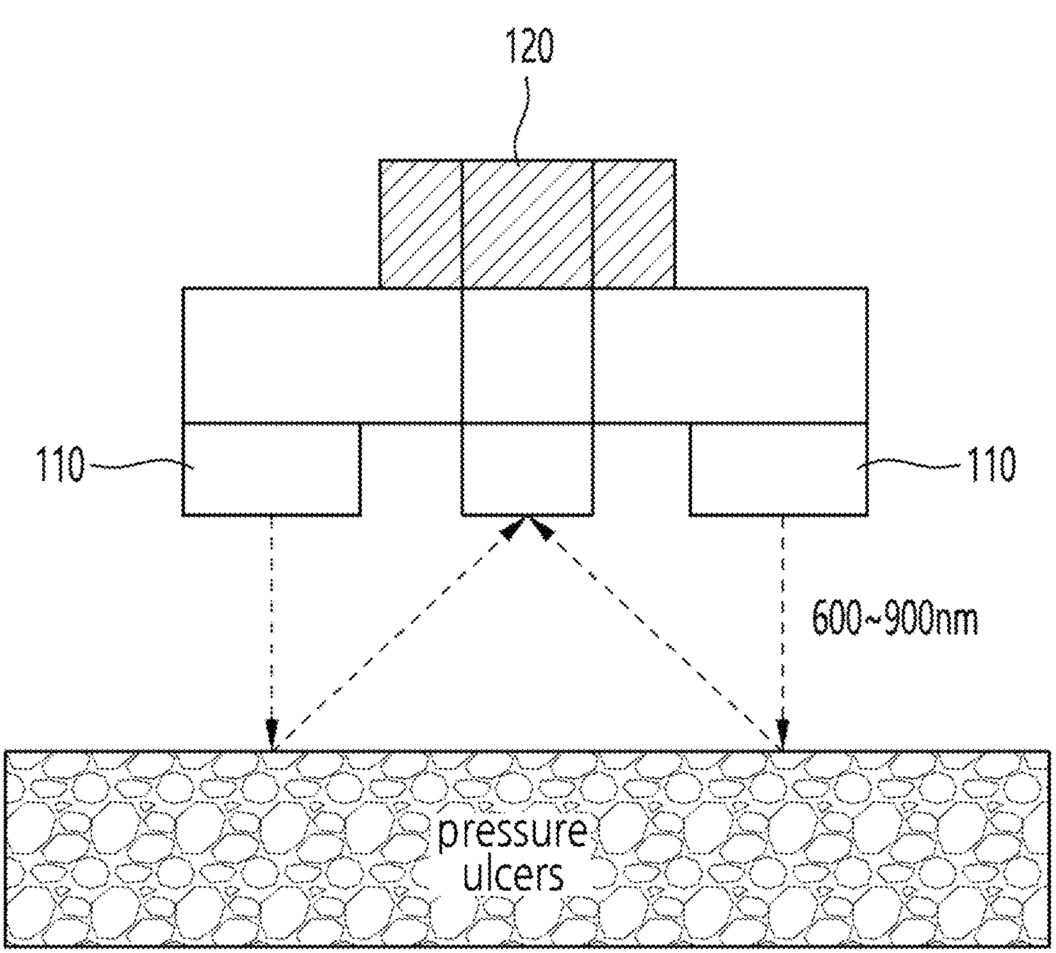
FIG. 5 is a view showing a schematic configuration of a measurement example of a depth data-based pressure ulcer diagnosis system using a multispectral light source according to an exemplary embodiment of the present disclosure.
Figure 6:
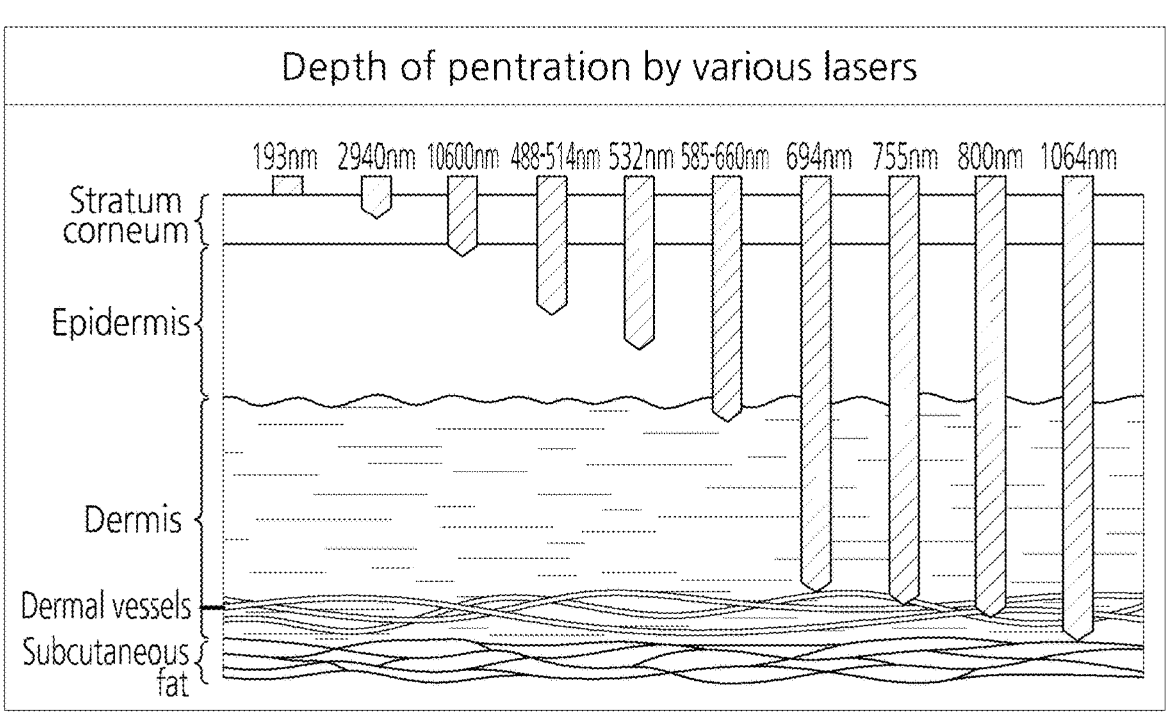
FIG. 6 is a view showing skin penetration per multispectral wavelength of a depth data-based pressure ulcer diagnosis system using a multispectral light source according to an exemplary embodiment of the present disclosure.

FIG. 5 is a view showing a schematic configuration of a measurement example of a depth data-based pressure ulcer diagnosis system using a multispectral light source according to an exemplary embodiment of the present disclosure, and FIG. 6 is a view showing skin penetration per multispectral wavelength of a depth data-based pressure ulcer diagnosis system using a multispectral light source according to an exemplary embodiment of the present disclosure.

The light emission unit 110 may be configured to emit light to the skin of the body part for assessing pressure ulcers. This light emission unit 110 may emit light to the skin of the body part for assessing pressure ulcers, and may be configured with a multi-wavelength light source device enabling the selective wavelength according to an absorption wavelength characteristic of biological tissues. Herein, the light emission unit 110 may be configured with the multi-wavelength light source device enabling the selective wavelength according to the absorption wavelength characteristic of biological tissues, and may be capable of emitting light with a wavelength of 600 to 900 nm. That is, as a technique for measuring the progression stage of pressure ulcers by using an optical principle regarding differences in transmittance per wavelength, the light emission unit 110 may function to obtain skin characteristics by emitting a multispectral light source to the same skin area.

In addition, as shown in FIG. 3, the light emission unit 110 may be configured to include a light source unit 111 that emits multispectral light sources of wavelengths different from each other to the same skin area for assessing pressure ulcers, a body unit 112 where the light source unit 111 is disposed for emitting multispectral light sources of wavelengths different from each other, and a controller 113 for controlling light radiation of the light source unit 111 disposed on the body unit 112 for emitting multispectral light sources of wavelengths different from each other. This light source unit 111 may be composed of a plurality of multispectral light sources capable of emitting multispectral light sources of a wide range of wavelengths from 600 to 900 nm.

In addition, the body unit 112 may be configured such that a plurality of multispectral light sources of the light source unit 111 are arranged, such that a hole may be formed so that the measurement unit 120 can be arranged in the central part where the plurality of multispectral light sources are arranged and reflected light can be measured through the measurement unit 120.

In addition, the controller 113 may be configured to control the light radiation of the light source unit 111 for emitting multispectral light sources of wavelengths different from each other, and may control to selectively emit multispectral light sources of wavelengths between 600 and 900 nm.

The measurement unit 120 may be configured to measure the light transmittance using the reflected light reflected when the light emission unit 110 emits light to the skin of the body part for assessing pressure ulcers. This measurement unit 120 may be configured to measure the light transmittance using the reflected light reflected when the light emission unit 110 emits light to the skin of the body part for assessing pressure ulcers and the light transmittance may be configured as depth data of skin characteristics per wavelength of multispectral light sources. That is, the measurement unit 120 may measure skin characteristics through the reflected light of the multispectral light source for selectively emitting according to the absorption wavelength characteristics of biological tissues within a wide range of wavelengths from 600 to 900 nm and may measure skin abnormalities caused by the pressure ulcer as depth data.

In addition, the measurement unit 120 may be configured with a depth camera for measuring depth data of skin characteristics per wavelength of the multispectral light sources of the light emission unit 110.

The pressure ulcer diagnosis unit 130 may be configured to assess the state of pressure ulcers on the basis of the light transmittance measured in the measurement unit 120. This pressure ulcer diagnosis unit 130 may assess the state of pressure ulcers on the basis of the light transmittance measured in the measurement unit 120 and may be capable of assessing pressure ulcers from depth data where the state of pressure ulcers is quantitatively assessed to determine a progression stage through big data learning utilizing the difference in light transmittance. That is, the transmittance of photons may change depending on the distribution of moisture or fat in the skin, so when pressure ulcers occur, skin necrosis may occur and the density of moisture and fat in the skin may be different from normal cells, which in turn shows light transmittance different from normal cells. The state of pressure ulcers in each stage may be quantitatively indicated through big data learning utilizing these light transmittance characteristics.

In addition, the pressure ulcer diagnosis unit 130 may assess pressure ulcers by quantitatively assessing the state of pressure ulcers to determine a progression stage through big data learning utilizing the difference in light transmittance and may be capable of non-invasively assessing the depth of the pressure ulcer incidence. Through this, it may function to visualize the progress of pressure ulcers in three dimensions more accurately than existing pressure ulcer diagnosis methods.

Figure 7:
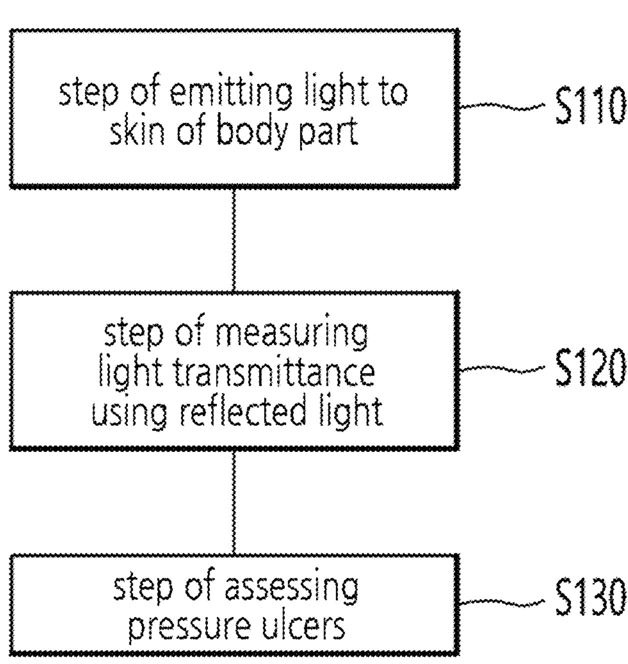
FIG. 7 is a view showing a flow of a depth data-based pressure ulcer diagnosis method using a multispectral light source according to an exemplary embodiment of the present disclosure.

FIG. 7 is a view showing a flow of a depth data-based pressure ulcer diagnosis method using a multispectral light source according to an exemplary embodiment of the present disclosure. As shown in FIG. 7, the depth data-based pressure ulcer diagnosis method using the multispectral light source according to an exemplary embodiment of the present disclosure may be implemented to include a step (S110) of emitting light to the skin of the body part for assessing pressure ulcers by a light emission unit 110, a step (S120) of measuring light transmittance by a measurement unit 120 using the reflected light reflected when the light emission unit 110 emits light to the skin of the body part for assessing pressure ulcers, and a step (S130) of assessing the state of pressure ulcers by a pressure ulcer diagnosis unit 130 on the basis of the light transmittance measured in the measurement unit 120.

In the step S110, the light emission unit 110 may emit light to the skin of the body part for assessing pressure ulcers. The light emission unit 110 in the step S110 may emit light to the skin of the body part for assessing pressure ulcers, and may be configured with a multi-wavelength light source device enabling the selective wavelength according to an absorption wavelength characteristic of biological tissues. Herein, the light emission unit 110 may be configured with the multi-wavelength light source device enabling the selective wavelength according to the absorption wavelength characteristic of biological tissues, and may emit light with wavelengths of 600 to 900 nm. That is, as a technique for measuring the progression stage of pressure ulcers by using an optical principle regarding differences in transmittance per wavelength, the light emission unit 110 may function to obtain skin characteristics by emitting multispectral light sources to the same skin area.

In addition, as shown in FIG. 3, the light emission unit 110 may be configured to include a light source unit 111 for emitting multispectral light sources of wavelengths different from each other to the same skin area for assessing pressure ulcers, a body unit 112 where the light source unit 111 is disposed for emitting multispectral light sources of wavelengths different from each other, and a controller 113 for controlling light radiation of the light source unit 111 disposed on the body unit 112 for emitting multispectral light sources of wavelengths different from each other. This light source unit 111 may be composed of a plurality of multispectral light sources capable of emitting the multispectral light sources of a wide range of wavelengths from 600 to 900 nm. In addition, the body unit 112 may be configured such that the plurality of multispectral light sources of the light source unit 111 are arranged, and a hole may be formed such that the measurement unit 120 can be arranged in the central part where the plurality of multispectral light sources are arranged and reflected light can be measured through the measurement unit 120. In addition, the controller 113 may configured to control the light radiation of the light source unit 111 for emitting multispectral light sources of wavelengths different from each other, and may be capable of controlling to selectively emit the multispectral light source of wavelengths between 600 and 900 nm.

In the step S120, the measurement unit 120 may measure the light transmittance using the reflected light reflected when the light emission unit 110 emits light to the skin of the body part for assessing pressure ulcers. This measurement unit 120 in the step S120 may measure the light transmittance using the reflected light reflected when the light emission unit 110 emits light to the skin of the body part for assessing pressure ulcers and the light transmittance may be configured as depth data of skin characteristics per wavelength of multispectral light sources. Herein, the measurement unit 120 may measure skin characteristics through the reflected light of the multispectral light source for selectively emitting according to the absorption wavelength characteristics of biological tissues within a wide range of wavelengths from 600 to 900 nm and may be capable of measuring skin abnormalities caused by the pressure ulcer as depth data. In this case, the measurement unit 120 may be configured with a depth camera for measuring depth data of skin characteristics per wavelength of the multispectral light sources of the light emission unit 110.

In the step S130, the pressure ulcer diagnosis unit 130 may assess the state of pressure ulcers on the basis of the light transmittance measured in the measurement unit 120. This pressure ulcer diagnosis unit 130 in this step S130 may assess the state of pressure ulcers on the basis of the light transmittance measured in the measurement unit 120 and may be capable of assessing the pressure ulcers from the depth data where the state of pressure ulcers is quantitatively assessed to determine a progression stage through big data learning utilizing the difference in light transmittance. That is, the transmittance of photons may change depending on the distribution of moisture or fat in the skin, so when pressure ulcers occur, skin necrosis may occur and the density of moisture and fat in the skin may be different from normal cells, which in turn shows light transmittance different from normal cells. The condition of each stage of pressure ulcers may be quantitatively indicated through big data learning utilizing these light transmittance characteristics. Herein, the pressure ulcer diagnosis unit 130 may assess pressure ulcers by quantitatively assessing the state of pressure ulcers to determine a progression stage through big data learning utilizing the difference in light transmittance and may be capable of non-invasively assessing the depth of the pressure ulcer incidence. Through this, it may function to visualize the progress of pressure ulcers in three dimensions more accurately than existing pressure ulcer diagnosis methods.

In this way, the depth data-based pressure ulcer diagnosis system and method using the multispectral light source may detect skin abnormalities caused by the pressure ulcer by using the optical principle that light has different characteristics per wavelength when penetrating the skin, such that skin characteristics are obtained by emitting the multispectral light source to the same skin area and skin abnormalities caused by the pressure ulcer are detected, thereby obtaining a wider range of bioanalysis and more accurate data by enabling selective wavelengths according to the absorption wavelength characteristics of biological tissues within a wide range of wavelengths from 600 to 900 nm.

As described above, the depth data-based pressure ulcer diagnosis system and method using the multispectral light source according to an exemplary embodiment of the present disclosure may be capable of detecting skin abnormalities caused by the pressure ulcer by using the optical principle of the difference in skin transmittance per wavelength of the multispectral light sources, by configuring to include the light emission unit for emitting light on the skin of the body part for assessing pressure ulcers, the measurement unit for measuring the light transmittance using the reflected light reflected when the light emission unit emits light to the skin of the body part for assessing pressure ulcers, particularly, may be capable of assessing pressure ulcers by quantitatively assessing the state of pressure ulcers to determine a progression stage through big data learning utilizing the difference in light transmittance on the basis of the optical principle that light has different characteristics per wavelength when penetrating the skin and non-invasively assessing the depth of the pressure ulcer incidence, by detecting skin abnormalities caused by the pressure ulcer by using the optical principle of the difference in skin transmittance per wavelength of the multispectral light sources, and additionally may be capable of representing the progress degree of pressure ulcers in three dimensions such that the probability of misdiagnosis of pressure ulcers can be reduced and the accuracy of the pressure ulcer diagnosis can be improved, by assessing pressure ulcers with the depth data standardized for the grade of pressure ulcers based on the difference in the light transmittance by using the optical principle of differences in skin transmittance per wavelength of the multispectral light sources.

The present disclosure described above may be modified or applied by those skilled in the art, and the scope of the technical idea according to the present disclosure should be defined by the following claims.

The invention claimed is:

1. A depth data-based pressure ulcer diagnosis system (100) using a multispectral light source, the system comprising:

- a light emission unit (110) for emitting light on skin of a body part for assessing pressure ulcers, the light emission unit (110) comprising;
- a body unit (112) having a central hole;
- a light source unit (111) including a plurality of multispectral light sources arranged on the body unit (112) around the central hole and configured to emit multispectral light having wavelengths different from each other within a range of 600 to 900 nm to the same skin area for assessing pressure ulcers; and
- a controller (113) configured to control light radiation of the plurality of multispectral light sources to selectively output the wavelengths different from each other according to an absorption wavelength characteristic of biological tissues;

a measurement unit (120) for measuring light transmittance using a reflected light reflected when the light emission unit (110) emits light to the skin of the body part for assessing pressure ulcers, the measurement unit (120) comprising a depth camera arranged at a central part of the body unit (112) corresponding to the central hole so that the reflected light from the same skin area is measured through the central hole, and being configured to configure the light transmittance measured for each of the wavelengths as depth data of skin characteristics per wavelength of the multispectral light; and a pressure ulcer diagnosis unit (130) being configured to:

(i) assess a state of a pressure ulcer on the basis of the depth data;

(ii) quantitatively assess the state of the pressure ulcer to determine a progression stage through big data learning utilizing a difference in the light transmittance;

(iii) non-invasively assess a depth of a pressure ulcer incidence; and (iv) represent a progress degree of the pressure ulcer in three dimensions using depth data standardized for a grade of pressure ulcers.

2. The system of claim 1, wherein the light emission unit (110) emits light to the skin of the body part for assessing pressure ulcers, and is configured with a multi-wavelength light source device enabling a selective wavelength according to an absorption wavelength characteristic of biological tissues.

3. The system of claim 2, wherein the light emission unit (110) is configured with the multi-wavelength light source device enabling the selective wavelength according to the absorption wavelength characteristic of biological tissues, and emits light with a wavelength of 600 to 900 nm.

4. The system of claim 1, wherein the light emission unit (110) comprises:

a light source unit (111) for emitting multispectral light sources of wavelengths different from each other to the same skin area for assessing pressure ulcers;

a body unit (112) where the light source unit (111) is disposed for emitting the multispectral light sources of wavelengths different from each other; and a controller (113) for controlling light radiation of the light source unit (111) disposed on the body unit (112) for emitting the multispectral light sources of wavelengths different from each other.

5. The system of claim 4, wherein the measurement unit (120) measures the light transmittance using the reflected light reflected when the light emission unit (110) emits light to the skin of the body part for assessing pressure ulcers and the light transmittance is configured as depth data of skin characteristics per wavelength of the multispectral light sources.

6. The system of claim 5, wherein the measurement unit (120) is configured with a depth camera for measuring depth data of skin characteristics per wavelength of the multispectral light sources of the light emission unit (110).

7. The system of claim 5, wherein the pressure ulcer diagnosis unit (130) assesses the state of pressure ulcers on the basis of the light transmittance measured in the measurement unit (120) and assesses pressure ulcers from depth data where the state of pressure ulcers is quantitatively assessed to determine a progression stage through big data learning utilizing a difference in the light transmittance.

8. The system of claim 7, wherein the pressure ulcer diagnosis unit (130) assesses pressure ulcers by quantitatively assessing the state of pressure ulcers to determine a progression stage through big data learning utilizing the difference in the light transmittance and non-invasively assesses a depth of a pressure ulcer incidence.

9. A depth data-based pressure ulcer diagnosis method using a multispectral light source, the method comprising:

(1) a step of emitting light on skin of a body part for assessing pressure ulcers by a light emission unit (110), the light emission unit (110) comprising a body unit (112) having a central hole, a light source unit (111) including a plurality of multispectral light sources arranged on the body unit (112) around the central hole and configured to emit multispectral light having wavelengths different from each other within a range of 600 to 900 nm to the same skin area for assessing pressure ulcers, and a controller (113) configured to control light radiation of the plurality of multispectral light sources to selectively output the wavelengths different from each other according to an absorption wavelength characteristic of biological tissues;

(2) a step of measuring light transmittance by a measurement unit (120) by using a reflected light reflected when the light emission unit (110) emits light to the skin of the body part for assessing pressure ulcers, the measurement unit (120) comprising a depth camera arranged at a central part of the body unit (112) corresponding to the central hole so that the reflected light from the same skin area is measured through the central hole and configuring the light transmittance measured for each of the wavelengths as depth data of skin characteristics per wavelength of the multispectral light; and (3) a step of assessing a state of pressure ulcers by a pressure ulcer diagnosis unit (130) on the basis of the light transmittance measured in the measurement unit (120), wherein the pressure ulcer diagnosis unit (130) assesses a state of a pressure ulcer on the basis of the depth data, including quantitatively assessing the state of the pressure ulcer to determine a progression stage through big data learning utilizing a difference in the light transmittance and non-invasively assessing a depth of a pressure ulcer incidence, and representing a progress degree of the pressure ulcer in three dimensions using depth data standardized for a grade of pressure ulcers.

10. The method of claim 9, wherein the light emission unit (110) emits light to the skin of the body part for assessing pressure ulcers, and is configured with a multi-wavelength light source device enabling a selective wavelength according to an absorption wavelength characteristic of biological tissues.

11. The method of claim 10, wherein the light emission unit (110) is configured with the multi-wavelength light source device enabling the selective wavelength according to the absorption wavelength characteristic of biological tissues, and emits light with a wavelength of 600 to 900 nm.

12. The method of claim 9, wherein the light emission unit (110) comprises:

a light source unit (111) for emitting multispectral light sources of wavelengths different from each other to the same skin area for assessing pressure ulcers;

a body unit (112) where the light source unit (111) is disposed for emitting the multispectral light sources of wavelengths different from each other; and a controller (113) for controlling light radiation of the light source unit (111) disposed on the body unit (112)

for emitting the multispectral light sources of wavelengths different from each other.

13. The method of claim 12, wherein the measurement unit (120) measures the light transmittance using the reflected light reflected when the light emission unit (110) emits light to the skin of the body part for assessing pressure ulcers and the light transmittance is configured as depth data of skin characteristics per wavelength of the multispectral light sources.

14. The method of claim 13, wherein the measurement unit (120) is configured with a depth camera for measuring depth data of skin characteristics per wavelength of the multispectral light sources of the light emission unit (110).

15. The method of claim 13, wherein the pressure ulcer diagnosis unit (130) assesses the state of pressure ulcers on the basis of the light transmittance measured in the measurement unit (120) and assesses pressure ulcers from depth data where the state of pressure ulcers is quantitatively assessed to determine a progression stage through big data learning utilizing a difference in the light transmittance.

16. The method of claim 15, wherein the pressure ulcer diagnosis unit (130) assesses pressure ulcers by quantitatively assessing the state of pressure ulcers to determine a progression stage through big data learning utilizing the difference in the light transmittance and non-invasively assesses a depth of a pressure ulcer incidence.

* * * * *